United States Patent [19]

Sagae

[11] 4,314,555
[45] Feb. 9, 1982

[54] INTRAVASCULAR CATHETER ASSEMBLY

[75] Inventor: Kyuta Sagae, Tokyo, Japan

[73] Assignee: Terumo Corporation, Tokyo, Japan

[21] Appl. No.: 118,310

[22] Filed: Feb. 4, 1980

[30] Foreign Application Priority Data

Feb. 20, 1979 [JP] Japan ............................ 54-20424[U]

[51] Int. Cl.³ .............................................. A61M 5/00
[52] U.S. Cl. .......................... 128/214.4; 128/DIG. 16
[58] Field of Search ............. 128/214.4, 214.2, 214 R, 128/221, DIG. 16, 349 R, 348

[56] References Cited

U.S. PATENT DOCUMENTS

| | | | |
|---|---|---|---|
| 1,087,845 | 2/1914 | Stevens | 128/214.4 UX |
| 3,662,752 | 5/1972 | Yokoyama | 128/214 R |
| 3,766,916 | 10/1973 | Moorehead et al. | 128/214.4 |
| 3,782,381 | 1/1974 | Winnie | 128/214.4 |
| 3,875,938 | 4/1975 | Mellor | 128/214.4 |
| 4,079,738 | 3/1978 | Dunn et al. | 128/214.4 |
| 4,192,305 | 3/1980 | Seberg | 128/349 R |
| 4,217,895 | 8/1980 | Sagae et al. | 128/214.4 |
| 4,243,034 | 1/1981 | Brandt | 128/221 X |

Primary Examiner—Gene Mancene
Assistant Examiner—Mickey Yu
Attorney, Agent, or Firm—Bacon & Thomas

[57] ABSTRACT

An intravascular catheter assembly which comprises:
 a flexible catheter tube whose proximal end is fixed to the distal end of a tubular hub of a catheter;
 a seal cap which is connected to the catheter hub with a flexible tube disposed between said seal cap and catheter hub and whose inner wall closely abuts against the outer wall of a cannula which guides the catheter through the blood vessel;
 a location bar which is fixed to a hub of the cannula and protrudes toward the distal end of the catheter; and
 a stopper which is mounted on the catheter hub to be engaged with the distal end of said location bar.

11 Claims, 12 Drawing Figures

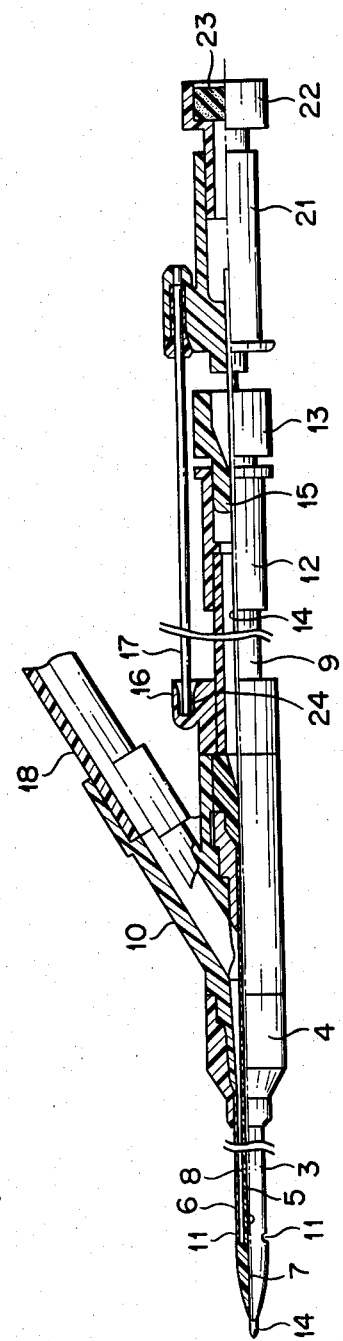
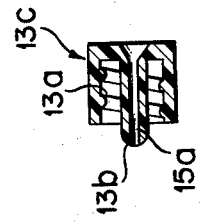
FIG. 6
FIG. 5
FIG. 4

F I G. 7
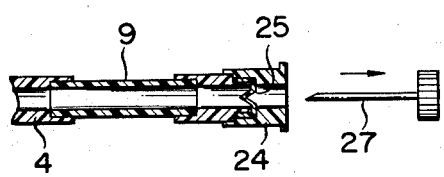
F I G. 8
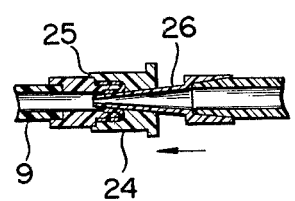
F I G. 9
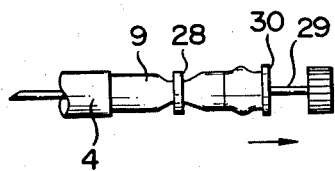
F I G. 10
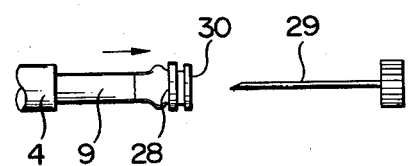
F I G. 11
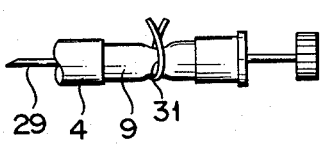
F I G. 12
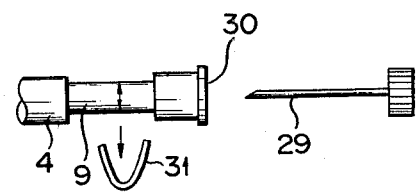

INTRAVASCULAR CATHETER ASSEMBLY

BACKGROUND OF THE INVENTION

This invention relates to an intravascular catheter assembly to be set in the blood vessel for the external blood circulation through a particular tube provided outside of the body of a patient or the administration of a medicinal liquid into his blood vessel.

An intravascular catheter is generally carried into the blood vessel with a cannula previously piercing the wall of the blood vessel used as a guide. If, in this case, the cannula is pulled out without applying any proper precautionary means after the insertion of the catheter into the blood vessel, the blood is liable to leak out through the catheter. To prevent this event, a thin-walled rubber cap has hitherto been fitted to the peripheral surface of the tubular hub of the conventional blood vessel catheter. The leakage of blood was prevented by piercing the cannula through the rubber cap.

Where, however, the intravascular catheter was assembled, the cannula was always made to pierce the rubber cap. Therefore, the sharp blade edge of the cannula was often damaged. Where the cannula was pushed through the wall of the blood vessel with the damaged blade edge of the cannula left intact, as is customarily the case, then there arose problems such as the increase of pain to a patient or injury to the blood vessel.

Further, the intravascular catheter was required to be fitted with, for example, another tubular member. In this case, the rubber cap fitted on the hub portion of the catheter with its flange turned back so as to prevent it from being removed at the time of the withdrawal of an inner needle had to be removed by being turned over, each time the tubular member was connected to the catheter. This removal operation was troublesome and time-consuming. Moreover, the rubber cap was not directly fitted around the hub of the catheter. Instead, the rubber cap was connected to the proximal end of the catheter hub with a flexible tube disposed between said rubber cap and catheter hub. Where, therefore, the cannula was pulled out of the rubber cap, the intervening flexible tube was undesirably elongated due to friction between the cannula and rubber cap, failing to ensure a safe operation.

Where the cannula was fitted to the catheter, the customary process of defining the position of the cannula so as to cause the distal end of the cannula to slightly protrude from the distal end of the catheter was (a) to form a stepped portion on the peripheral surface of the cannula and also a stepped portion on the inner wall of the hub and cause both stepped portions to engage each other, or (b) to provide one end of the cannula with a cylindrical portion capable of being fitted around the peripheral surface of the aforesaid intervening flexible tube, fit a bayonet prop to the proximal end of the cylindrical portion, provide bayonet pawls on the peripheral surface of the hub and cause the bayonet prop to be engaged with the bayonet pawls.

However, with the above-mentioned known cannula-locating process of forming a stepped portion on the peripheral surface of the cannula, the stepped portion of the cannula strikes against the stepped portion formed on the inner wall of the blood passage of the hub, tending to damage the stepped portion of the hub. Moreover, the blood is liable to be stagnantly gathered around the stepped portion of the hub in the vortical form, and consequently flow is retarded. This event sometimes gives rise to the coagulation of the blood. Further, the proximal end of the cannula which was provided with a stepped portion had a larger diameter than the distal end thereof, thereby resulting in an increase in the resistance which was applied to the removal of the rubber cap and consequently the greater elongation of the aforesaid flexible intervening tube.

With the prior art bayonet type cannula-locating process, the bayonet pawls protruding from the peripheral surface of the hub bite into the skin of, for example, a patient, when the catheter is fixed to his body, thus imparting unnecessary pains to him. Further drawbacks of this bayonet type cannula-locating process were that the cannula had to be rotated, each time it was taken into and out of the patient's body, tending to injure his blood vessel, and moreover, the insertion and removal of the cannula always involved complicated steps and consumed much time.

SUMMARY OF THE INVENTION

This invention has been accomplished in view of the above-mentioned circumstances, and is intended to provide an intravascular catheter which can be assembled without damaging the sharp blade edge of the cannula and can be operated easily and safely without the possibility of blood leaking out.

To this end, the present invention provides an intravascular catheter assembly, which comprises:

a flexible catheter tube which is provided with an axially extending hole and whose proximal end is fixed to the distal end of a hub of a catheter;

a cannula whose distal end is detachably inserted into the axially extending hole to protrude from the distal end of the flexible catheter tube, as need arises, and whose proximal end is fixed to the distal end of the hub;

a connector coupled to the proximal end of the catheter hub with a flexible tube interposed between said catheter hub and connector;

a seal cap which is fitted around the connector, and provided with an axially extending hole penetrating the cannula, and whose inner wall closely abuts against the outer wall of the cannula when it passes through the axially extending hole;

a cannula-locating bar, one end of which is fixed to the hub of the cannula and the other end of which protrudes toward the distal end of the catheter; and a stopper which is mounted on the peripheral surface of the tubular catheter hub to abut against the distal end of the cannula-locating bar, thereby defining the extent to which the cannula is inserted into the catheter tube.

BRIEF DESCRIPTION OF THE DRAWINGS

FIGS. 1 to 12 jointly indicate an intravascular catheter assembly embodying this invention.

FIG. 1 is a lateral view of the intravascular catheter assembly;

FIG. 2 is a lateral view of the catheter section of FIG. 1;

FIG. 3 is a lateral view of the cannula section of FIG. 1;

FIG. 4 is a partially sectional view of the assembly of FIG. 1;

FIG. 5 is a sectional view of a seal cap;

FIG. 6 is a sectional view of one modification of the seal cap;

FIGS. 7 and 8 are sectional views of another modification of the seal cap;

FIGS. 9 and 10 are side views of the main part of a flexible tube-blocking means provided at the proximal end of the catheter section of FIG. 1; and FIGS. 11 and 12 are side views of the main part of a modification of the flexible tube-blocking means of FIGS. 9 and 10.

DETAILED DESCRIPTION OF THE PREFERRED EMBODIMENTS

Figure 1:
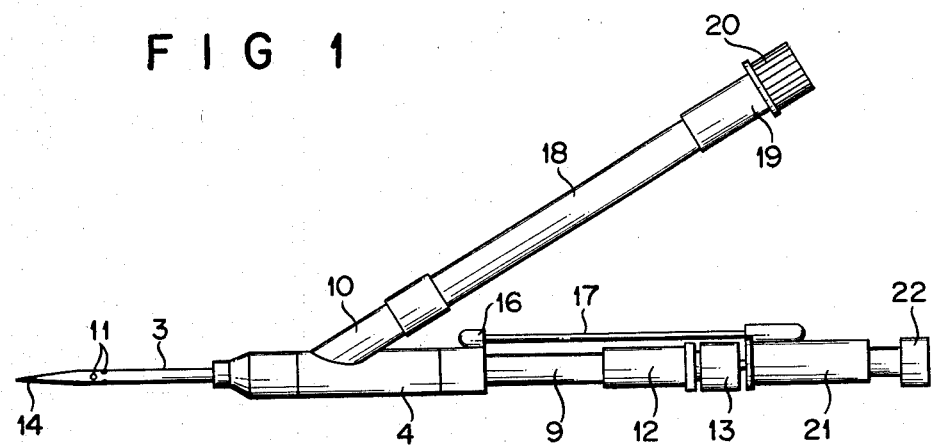
Figure 2:
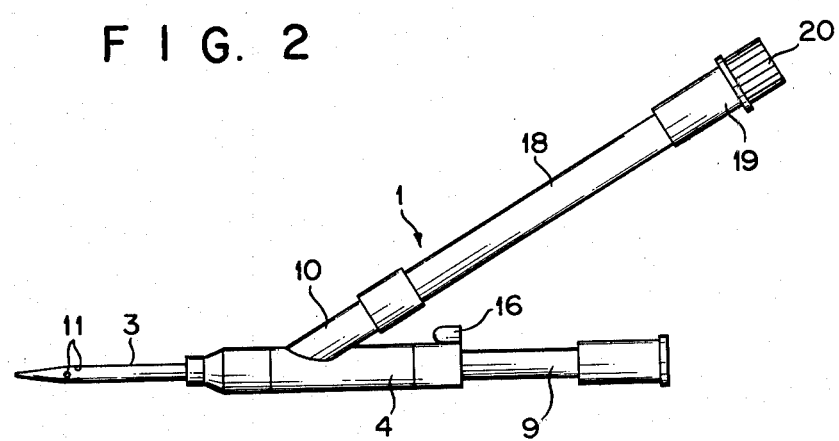
Figure 3:
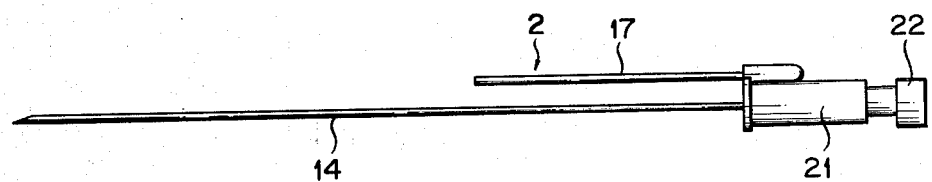

There will now be describe by reference to the accompanying drawings an intravascular catheter assembly embodying this invention. FIG. 1 is a lateral view of the intravascular catheter assembly of the invention which comprises the catheter section 1 of FIG. 2 and the cannula section 2 of FIG. 3. The catheter section 1 comprises a catheter tube 3 prepared from a transparent or translucent material such as fluorine series resin and a hub 4 prepared from, for example, a thermoplastic resin such as polycarbonate or polypropylene. As seen from FIG. 4, the catheter tube 3 is formed as a double-tube, that is, an inner tube 5 and an outer tube 6. The inner wall of the inner tube 5 defines an inner chamber 7. An annular chamber 8 is defined by the outer wall of the inner tube 5 and the inner wall of the outer tube 6.

The inner chamber 7 is surrounded by the hub 4 and communicates with the later described transparent or translucent flexible tube 9 prepared from, for example, soft polyvinyl chloride. The annular chamber 8 communicates with a branch tube 10 diverging from the hub 4.

The outer tube 6 of the double-walled catheter tube 3 is provided with a plurality of small holes 11 which communicate with the interior of the annular chamber 8. Where the cannula 14 is inserted into the catheter tube 3 with the blade plane of the cannula 14 turned upward, then the small holes 11 should preferably be formed on the lateral or bottom wall of the outer tube 6 of the catheter tube 3. The reason for this is that where the catheter tube 3 is inserted through the wall of the blood vessel, it is desired to avoid the occurrence of difficulties in said insertion or any increase of insertion resistance which might otherwise result due to the skin of the blood vessel being caught in said small holes 11.

Fitted to the proximal end of the aforesaid transparent or translucent flexible tube 9 is a transparent or translucent connector 12 to which a seal cap 13 is detachably attached. A seal cap 13 is prepared from synthetic resin such as soft or hard polyvinyl chloride and has an axially extending hole 15 which allows for the passage of the later described cannula 14, and whose inner wall tightly abuts against the outer wall of the cannula 14.

The hub 4 of the catheter tube 3 is provided with a stopper 16 which projects toward the branch tube 10. The free end of a cannula-locating bar 17 included in the cannula assembly 2 bears against the stopper 16 as later described. Connected to the outer end of the branch tube 10 is a soft tube 18 prepared, for example, from polyvinyl chloride. The outer end of said soft tube 18 is fitted with a transparent or translucent connector 19 (FIG. 2), to which the ordinary cap 20 is attached.

Fixed to the proximal end of the cannula 14 is a transparent tubular hub 21 whose interior communicates with the opening of the cannula 14. The proximal end opening of the hub 21 is fitted with a cap 22 which is provided with a blood leakage-preventing filter 23 (FIG. 4). The interior of the hub 21 communicates with the open air through said filter 23. Fitted to the hub 21 of the cannula 14 is the cannula-locating bar 17 which extends in parallel with the cannula 14 toward the distal end thereof. Where the cannula 14 is inserted into the catheter assembly 1, the distal end of the cannula-locating bar 17 abuts against the stopper 16, thereby defining the extent to which the cannula 14 is inserted into the catheter tube 3 and consequently causing the blade section of the distal end portion of the cannula 14 always to project from the distal end of the catheter tube 3. The stopper 16 is provided with a cavity 24 into which the distal end of the cannula-locating bar 17 is inserted. This insertion fixes the position of said cannula-locating bar 17, preventing the rotation of the cannula hub 21. As a result, the blade plane of the cannula 14 takes a fixed position relative to the catheter assembly 1. In other words, where the cannula 14 pierces the wall of the blood vessel with the blade plane of said cannula 14 turned upward, then the branch tube 10 is always set in a direction substantially perpendicular to that in which the cannula 14 is inserted through the wall of the blood vessel.

There will now be described the manner in which the intravascular catheter is practically applied. Before the catheter assembly 1 is made to pierce the wall of the blood vessel, the cannula assembly 2 is received in said catheter assembly 1. Thus both assemblies 1, 2 are used in a body. At this time, the cannula 14 of the cannula assembly 2 is inserted into the axially extending hole 15 of the seal cap 13. Where the cannula 14 passes through the flexible tube 9 and the inner chamber 7 until the distal end portion of the cannula 14 slightly protrudes from the distal end of the catheter tube 3 as shown in FIG. 1, then the cannula-locating bar 17 is brought to rest due to its distal end abutting against the stopper 16. Since, at this time, the distal end of the cannula-locating bar 17 is fitted into the cavity 24 of the stopper 16, the cannula hub 21 is prevented from being rotated. In other words, the blade plane of the cannula 14 takes the prescribed position relative to the catheter assembly 1, and consequently to the plural small holes 11 formed in the outer tube 6 of the double-walled catheter tube 3 as well as to branch tube 10. Therefore, the cannula 14 can easily pierce the wall of the blood vessel in a proper state.

The exposed distal end blade section of the cannula 14 pierces the wall of the blood vessel in the same direction as that in which the blood flows. When the cannula 14 is fully inserted into the blood vessel, the blood runs through the cannula 14 upto the hub 21. Since the hub 21 is transparent or translucent, the blood can be easily observed from the outside, making it possible to determine whether the distal end of the cannula 14 has been assuredly inserted into the blood vessel.

After the insertion of the cannula 14 into the blood vessel has been confirmed, the small holes 11 formed in the outer tube 6 of the double-walled catheter tube 3 are brought into the blood vessel. At this time, the blood flows into the annular chamber 8 of the catheter tube 3 through the small holes 11. Said flow of the blood can be recognized through the transparent or translucent catheter tube 3 and the hub 4.

The hub 4 of the catheter assembly 1 is held by one hand, and the cannula assembly 2 is gripped by the other hand. Under this condition, the cannula 14 is gently pulled backward with the catheter tube 3 kept in position. The distal end of the cannula 14 is temporarily brought to rest, immediately before the proximal end of the cannula 14 reaches the seal cap 13. At this time, the axially extending hole 15 of the seal cap 13 is fully plugged with the cannula 14. The intermediate part of the flexible tube 9 is tightly clamped by the fingers or forceps. The seal cap 13, together with the cannula assembly 2, is taken out of the connector 12 of the catheter assembly 1, with the flexible tube 9 left thus clamped. Since, at this time, the flexible tube 9 is tightly blocked, the blood does not leak out even when the seal cap 13 and cannula 14 are taken off.

Thereafter, the blocked tube 9 is slightly opened by reducing the force with which said tube 9 is clamped by the fingers or forceps. As a result, the connector 12 is fully filled with blood. After the connector 12 is fully filled with blood, the flexible tube 9 is tightly blocked. Since the connector 12 has a small diameter, the blood is safely kept within said connector 12 due to its surface tension and does not leak out of the connector 12.

Therefore, one end of, for example, a blood circulation passage is fitted to the connector 12. Since, at this time, the connector 12 is fully filled with blood, air is prevented from being brought in, when the terminal of the blood circulation passage is put into the connector 12. In other words, when the blood circulation passage is connected to the catheter assembly 1, air does not enter the catheter assembly and consequently is prevented from flowing through the blood vessel.

The other terminal of the blood circulation passage is connected to the branch tube 10, after the cap thereof 20 is taken off.

As previously described, the distal end of the catheter 3 pierces the wall of the blood vessel in the same direction as that in which the blood flows. Therefore, the distal end opening of the inner chamber 7 defined by the inner wall of the inner tube 5 lies downstream of that portion of the wall of the blood vessel which is pierced by the catheter 3. The small holes 11 communicating with the interior of the outer annular chamber 8 are positioned upstream of said pierced portion of the blood vessel. In other words, the outer annular chamber 8 is used as the blood influx section, and the inner chamber 7 is applied as the blood efflux section. Thus, the blood is taken out of the blood vessel at said upstream section and is returned to the blood vessel at said downstream section. Consequently, the blood which has flowed through the blood circulation passage is prevented from running backward to be mixed with the incoming streams of blood. Since the catheter tube 3 is provided with the inner and outer annular chambers 7, 8, the above-mentioned desirable effect can be ensured simply by selecting only the direction in which the catheter tube 3 pierces the wall of the blood vessel.

Even where the catheter tube 3 is made to pierce the wall of the blood vessel in a direction opposite to that in which the blood flows, then the aforesaid favorable effect is also realized by using the inner chamber 7 as the blood efflux section and the outer annular chamber 8 as the blood influx section.

This invention is not limited to the foregoing embodiment, but may be applied in various modifications. For instance, the seal cap (FIG. 5) may be replaced by a seal cap 13c of FIG. 6 which is prepared from soft polyvinyl chloride, whose inner wall is provided with screw grooves 13a, and whose axial section is formed into a tubular projection 13b. In this case, the cannula 14 slides through the axially extending hole 15a of the tubular projection 13b. The seal cap 13c can be securely set in place by engagement with the flanged section of the connector 12. Further, the seal cap 13c which is prepared from soft polyvinyl chloride can be removed simply by being forcefully pulled without being rotated.

A seal cap used with this invention need not be the type which is always left open at both ends, but may be the type which is normally elastically closed and forced open by the insertion of the cannula 14. FIGS. 7 and 8 illustrate the concrete examples of the latter type. Referring to FIG. 7, a rubber seal member 25 is fitted to the tubular connector 24 attached to the proximal end of the flexible tube 9. The seal member 25 is formed of an elastic attachment which elastically projects into the interior of the tubular connector 24 and normally remains closed. As shown in FIG. 8, the seal member 25 allows for the insertion of the terminal of the blood circulation passage into the tubular connector 24. Obviously as seen from FIG. 7, the seal member 25 allows for the insertion of the cannula 27. According to the embodiment of FIGS. 7 and 8, the seal member 25 can be automatically blocked simply by pulling out the cannula 27 without clamping the flexible tube 9 by the fingers or forceps. The seal member 25 according to the embodiment of FIGS. 7 and 8 dispenses with the clamping of said flexible tube 9 by the fingers or forceps and can be operated with great ease. Moreover, the seal member 25 is automatically blocked, suppresses the leakage of blood, and consequently allows for the clean handling of the catheter. Further, where the terminal 26 of the blood circulation passage is connected to the connector 24 as shown in FIG. 8, the seal member 25 is automatically opened and a passage is formed, thereby eliminating the necessity of carrying out any particular operation of blocking the seal member 25, and effectively suppressing the leakage of blood.

The flexible tube 9 can be blocked by various different processes from the above-mentioned clamping by the fingers or forceps. With a seal member according to the embodiment of FIG. 9, an elastic ring 28 is fitted around the peripheral wall of the intermediate part of the flexible tube 9 to block it by the elasticity of said ring 28. Where, with the embodiment of FIG. 9, the cannula 29 is pulled out, then the flexible tube 9 is automatically blocked to suppress the leakage of blood. Where the terminal of the blood circulation passage is connected to the connector 30, then the elastic ring 28 is shifted to the peripheral wall of the connector 30 to release the flexible tube 9 from a blocked state for communication with the blood circulation passage.

With a seal member according to the embodiment of FIG. 11, a clamping member 31 formed by bending an elastic bar into the V-shape replaces the elastic ring 28 of FIGS. 9 and 10. As shown in FIG. 12, the V-shaped clamp 31 can be taken off the intermediate part of the flexible tube 9 by being pulled crosswise.

Where the catheter and cannula are assembled together, this invention eliminates, as described above, the necessity of letting the blade of a cannula pierce, for example, a rubber cap. Therefore, the cannula undergoes very little resistance when inserted into the blood vessel, and can be easily taken into and out of the blood vessel. Consequently, the sharp blade edge of the cannula is saved from damage and imparts little pain to a patient.

Further according to this invention, the means for defining the position of the cannula relative to the catheter is provided outside of a blood passage, little damaging its inner wall and exerting no harmful effect on the blood. Moreover, the cannula-locating means need not be operated by rotation or by any other complicated process, but can be handled easily and safely.

Throughout the foregoing embodiments, the description refers to the case where the intravascular catheter was formed of a double tube. However, this invention need not be restrictively applied to said type of catheter, but obviously can be applied to a single tube type catheter.

What is claimed is:

1. An intravascular catheter assembly which comprises:

a catheter hub;

a flexible catheter tube which is provided with an axially extending hole, and whose proximal end is fixed to said catheter hub;

a cannula which is detachably inserted into the axially extending hole, with the distal end of said cannula arranged to protrude from the distal end of the flexible catheter tube and the proximal end of said cannula being provided with a tubular hub;

a rigid connector which is fitted to the proximal end of the catheter hub with a flexible tube interposed between said connector and the catheter hub;

a seal cap which is fitted around the connector, the an axially extending hole, and whose inner wall tightly abuts against the outer wall of the cannula when the cannula passes through said axially extending hole;

a cannula-locating bar, one end of which is fixed to the peripheral surface of a tubular hub of the cannula, and the other end of which projects toward the proximal end of the catheter hub; and a stopper which is mounted on the peripheral surface of the catheter hub to abut against the distal end of the cannula-locating bar, thereby defining the extent to which the cannula is inserted into the catheter tube.

2. The intravascular catheter assembly according to claim 1, wherein the flexible catheter tube is formed of a double tube which has an axially extending hole and an outer annular hole defined around said axially extending hole; the distal end of said outer annular hole is blocked; at least one small hole is formed in the blocked portion of the outer annular hole; and the proximal end of the outer annular hole communicates with a branch tube diverted from the peripheral surface of the tubular hub of the flexible catheter tube.

3. The intravascular catheter assembly according to claim 1 or 2, wherein the catheter tube is transparent or translucent.

4. The intravascular catheter assembly according to claim 1 or 2, wherein the connector is coupled to the proximal end of the tubular hub of the catheter with a transparent or translucent tube disposed between said connector and catheter hub.

5. The intravascular catheter assembly according to claim 1 or 2, wherein the connector is transparent or translucent.

6. The intravascular catheter according to claim 1 or 2, wherein the opening of the tubular hub of the cannula is fitted with a detachable cap provided with a filter.

7. The intravascular catheter assembly according to claim 1 or 2, wherein the tubular hub of the cannula is transparent or translucent.

8. The intravascular catheter assembly according to claim 1 or 2, wherein the seal cap has a narrow hole whose inner wall tightly abuts against the outer wall of the cannula when it is inserted into that portion of the seal cap which is engaged with the connector; a broad hole is formed on the opposite side of the seal cap to the narrow hole; and the intermediate portion of the axially extending hole between the small and large diameter sections is tapered.

9. The intravascular catheter assembly according to claim 1 or 2, wherein the seal cap is formed of soft plastics material, and comprises an outer annular wall surrounding the peripheral surface of the connector and a tube which extends through the axial section of the outer annular wall and has a narrow hole whose inner wall tightly abuts against the outer wall of the cannula; and an annular groove is defined between the inner surface of the outer annular wall and the outer surface of the axially extending tube to allow for the insertion of the opening of the connector.

10. The intravascular catheter assembly according to claim 1 or 2, wherein the seal cap has an axially extending hole allowing for a insertion of the terminal of a blood circulation passage; and the proximal end of the axially extending hole is provided with an elastic membrane which allows for the insertion of the cannula or the terminal of the blood circulation passage, and obstructs the flow of blood when the cannula or the terminal of the blood circulation passage is pulled out.

11. The intravascular catheter assembly according to claim 1 or 2, which further comprises clamping means for tightly holding a flexible tube provided between the tubular hub of the catheter and the connector.

* * * * *